United States Patent [19]

Marini et al.

[11] 4,443,402
[45] Apr. 17, 1984

[54] METHOD AND APPARATUS FOR DETECTING DEFECTIVE FUEL ELEMENTS IN A NUCLEAR REACTOR FUEL ASSEMBLY

[75] Inventors: Jean Marini, Marly le Roi; Alain Gravelle, Le Plessis Robinson, both of France

[73] Assignee: Framatome, Courbevoie, France

[21] Appl. No.: 310,268

[22] Filed: Oct. 9, 1981

[30] Foreign Application Priority Data

Oct. 24, 1980 [FR] France .................... 80 22789

[51] Int. Cl.³ ............................. G21C 17/00
[52] U.S. Cl. ............................ 376/252
[58] Field of Search ........................ 376/252

[56] References Cited

U.S. PATENT DOCUMENTS

| | | | |
|---|---|---|---|
| 3,901,090 | 8/1975 | Akey et al. | 376/245 |
| 3,936,348 | 2/1976 | Wachter et al. | 376/252 |
| 3,945,245 | 3/1976 | Stehle et al. | 376/252 |
| 4,016,749 | 4/1977 | Wachter | 376/252 |
| 4,126,514 | 11/1978 | Wonn | 376/252 |
| 4,193,843 | 3/1980 | Womack et al. | 376/252 |
| 4,366,711 | 1/1983 | Weilbacher et al. | 376/252 |

FOREIGN PATENT DOCUMENTS

| | | | |
|---|---|---|---|
| 26711 | 8/1981 | European Pat. Off. | 376/252 |
| 51016 | 5/1982 | European Pat. Off. | 376/252 |
| 2505645 | 8/1976 | Fed. Rep. of Germany | 376/252 |

Primary Examiner—Sal Cangialosi
Attorney, Agent, or Firm—Pollock, Vande Sande & Priddy

[57] ABSTRACT

Method and apparatus for detecting defective fuel elements in a nuclear reactor assembly. The assembly (20) is kept entirely immersed in a liquid such as water, ultrasonic waves are propagated successively in each of the fuel elements of the assembly or rods (21), an ultrasonic sensor (25) is disposed near the assembly (20) and the waves which may be scattered into the protective liquid by the defects in the fuel rod are picked up to determine the presence of a defective assembly and locate the defective rod in the assembly. The invention is particularly applicable to fuel assemblies of a pressurized water nuclear reactor.

8 Claims, 4 Drawing Figures

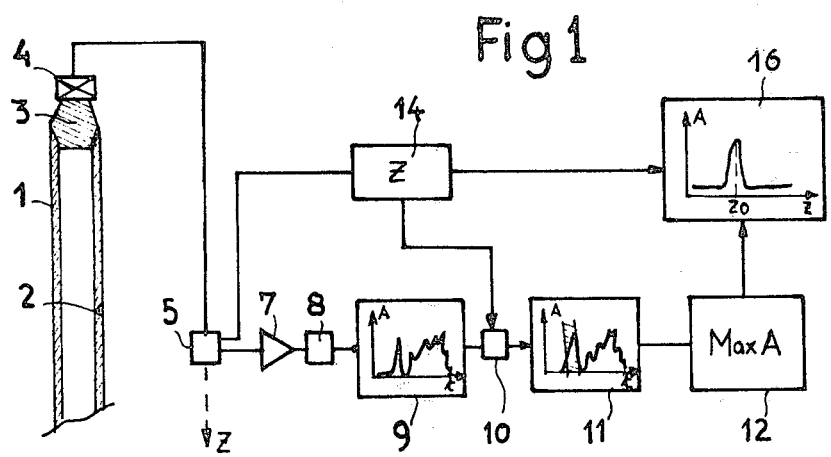
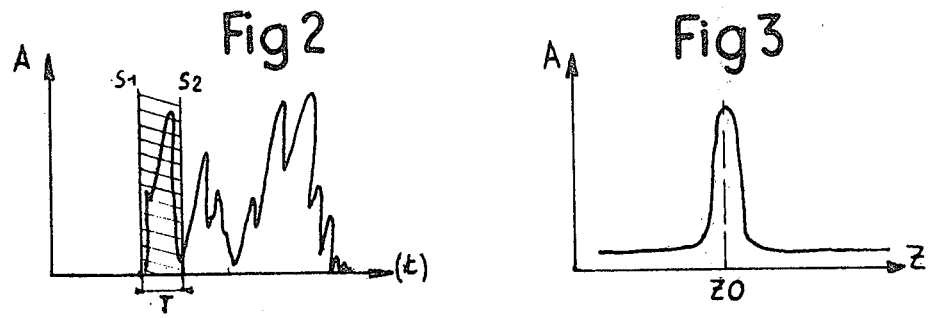
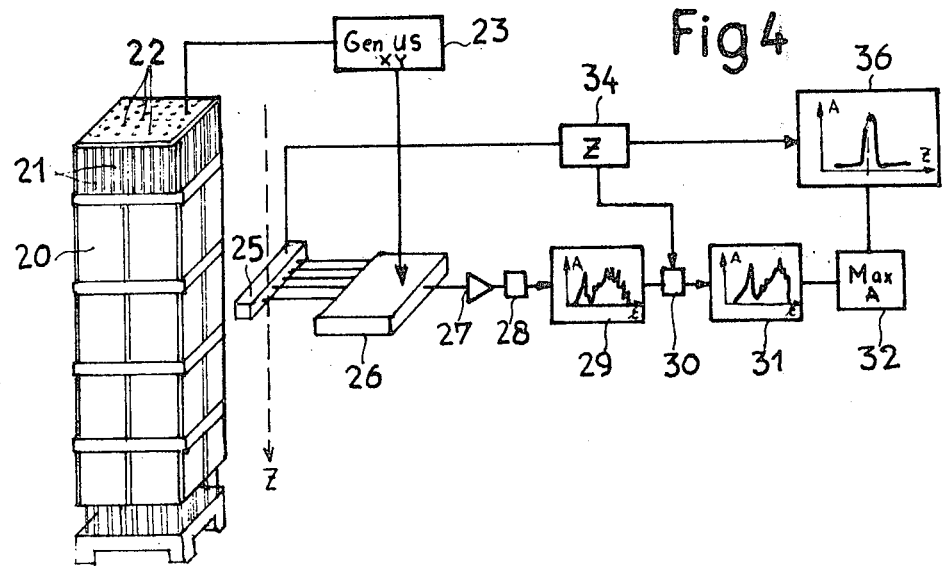

METHOD AND APPARATUS FOR DETECTING DEFECTIVE FUEL ELEMENTS IN A NUCLEAR REACTOR FUEL ASSEMBLY

FIELD OF THE INVENTION

The invention concerns a method and apparatus for detecting defective fuel elements in a fuel assembly for a nuclear reactor.

BACKGROUND

Fuel assemblies for a nuclear reactor, particularly fuel assemblies for a pressurized water nuclear reactor, are constituted by a bundle of elongate fuel elements termed fuel rods, arranged parallel to each other in the longitudinal direction of the assembly.

These fuel rods are constituted by tubes made of cladding material filled with fuel pellets.

The different fuel rods are held in position in the assembly by spacer plates and end plates connected to support tubes in place of some fuel rods and allowing the rigidity of the assembly to be assured.

During use in the core of the nuclear reactor, these assemblies can deteriorate under the action of various mechanical or thermal stresses or under the action of corrosion, so that the cladding material of the fuel rods can present fissures through which radio active material can pass into the cooling fluid of the reactor.

When the nuclear reactor is reloaded, during which operation used assemblies located in one part of the core are replaced by new assemblies, it is necessary to detect assemblies including leaking fuel rods.

During these operations, the core of the reactor is entirely immersed in a protective liquid such as water, and the assemblies involved in the reloading operations are conveyed under water from the vessel of the reactor to the fuel pond.

Leaking assemblies must be detected and these assemblies put in a region of the core in which reloading is taking place or in a region of the core in which assemblies are kept ready.

it is in fact essential to replace these leaking assemblies by new assemblies or to replace the defective rods inside the assembly by new rods.

When the assembly must definitely be replaced by a new assembly, it is still essential to know whether the used assembly is leaking, since, if this is the case, special precautions must be taken for moving or storing it.

To carry out the detection of a leaking assembly, the use of the apparatuses termed "crack detection cells" has been proposed, in which assemblies are disposed successively, one by one, inside the fuel pond. The temperature of the assembly is raised so that the pressure of the fission gases contained in the fuel rods increases and these gases escape inside the crack detection cell via the fissures in the rods, if these are defective.

Measurement of gamma activity in the fluid occupying the crack detection cell allows the escape of fission gas and hence the presence of a defective assembly, to be detected.

Such a crack detection cell is described in FRAMATOME French Pat. No. 2.389.202.

There is also a known method of detecting leaking fuel assemblies using sonic or ultrasonic acoustic phenomena connected with the impact of fission gas bubbles on a screen or with the build-up of the fission gases leaving the fuel rods through the faults in the cladding under the surface of the screen.

To implement this method, the gases must be expanded by heating or depressurizing of the assembly. These two methods of finding defective assemblies which are simple to implement and integrate perfectly with operations for transferring fuel allow defective assemblies to be determined during these transfer operations. But these methods do not allow the leaking fuel rod to be exactly located inside the assembly.

The defective fuel rods must obviously be identified when these rods are required to be replaced in the assembly by new rods before the assembly is reloaded in the core of the reactor.

Methods have therefore been proposed which allow defective fuel rods to be identified in assemblies during reloading operations on the nuclear reactor. For example, French Pat. No. 2.222.732, discloses detection of the presence of water in defective fuel rods by heating each of the rods of the assembly by induction and detecting bubbles of vapor or condensation which can occur at the cap of the fuel rod, by means of an ultrasonic echo test.

This method, which allows leaking fuel rods to be located, does necessitate partial dismantling of the assembly since each rod must be placed inside an apparatus for induction heating.

It has also been proposed, in French Pat. No. 2.287.753, to propagate an acoustic signal along the cladding of each of the fuel elements and pick up the signal obtained after propagation along the cladding of the fuel elements. When there is a defect in the cladding, an attenuation of the signal is observed, due to the presence of this defect.

To implement this method, an emitter and a receiver of acoustic waves must be placed on each rod, and the outer surface of the cladding of the fuel rod must be isolated from the cooling fluid, by placing the rod in a gaseous atmosphere.

Also, when the defect to be detected is at a distance from the end where the acoustic wave receiver is located, there is a risk of the return signal being drowned in the acoustic background noise.

There is therefore no known method allowing very reliable and easily implemented detection of defective fuel rods in an assembly which has not been dismantled.

SUMMARY OF THE INVENTION

The object of the invention is a method of detecting defective fuel elements in a nuclear reactor fuel assembly constituted by a bundle of elongate fuel elements or rods arranged parallel to each other in the longitudinal direction of the assembly, by detection of possible anomalies in the propagation of ultrasounds in the fuel rods, this detection method, which is very easily implemented, allowing reliable detection of defective fuel rods without dismantling the fuel assembly.

To implement the method according to the invention:

the assembly is kept entirely immersed in a protective liquid, such as water, ultrasonic waves are propagated in each of the fuel rods of the assembly successively, over their whole length from one of their ends, an ultrasonic sensor is disposed near the fuel rods of the assembly, the ultrasonic waves which may be scattered by the defects in the fuel rods into the protective liquid in which the assembly is immersed are picked up and, if such scattered waves are picked up, the presence of at least one defect in the rod in which the ultrasounds are propagated is thus determined.

To provide a full understanding of the invention, an example of implementation of the method according to the invention will now be described, by way of non-limiting example, with reference to the attached drawings, in the case of the testing of fuel assemblies of a pressurized water nuclear reactor in the swimming pool of the reactor or in the fuel pond, with locating of the defect on the fuel rod.

BRIEF DESCRIPTION OF THE DRAWINGS

FIG. 1 represents diagrammatically the equipment used for measurement on a fuel rod.

FIG. 2 represents the ultrasonic signal picked up by the testing equipment.

FIG. 3 represents the variations in the maximum amplitude of the signal as a function of the position of the sensor along the length of the fuel rods.

FIG. 4 represents the equipment used for testing a complete assembly.

DETAILED DESCRIPTION

FIG. 1 shows a fuel rod 1 whose cladding has a fissure 2.

The upper end of the rod is closed by a cap 3, with an ultrasonic generator 4 disposed in contact, producing ultrasonic waves which are propagated in the whole fuel rod from the end represented in FIG. 1 to its opposite end.

The fuel rod 1 is entirely immersed in the water which fills the fuel pond.

An ultrasonic sensor 5 is disposed near the lateral surface of the rod 1, connected to a vertical displacement apparatus allowing it to take up any position along the length of the rods.

Z designates the displacement axis of the sensor 5 which, in the case of the apparatus represented in FIG. 1, corresponds to the vertical direction.

A connection between the ultrasonic generator 4 and the sensor 5 allows the time of emission of an ultrasonic wave to be established as time origin for the sensor 5.

FIG. 2 shows the signal picked up by the sensor 5 in the case of an ultrasonic wave being emitted by the generator 4.

This signal S can be resolved into two signals S1 and S2.

The signal S1 corresponds to the ultrasonic waves scattered at the defect 2 into the water surrounding the rod while the signal S2 corresponds to interference signals which arrive at the sensor 5 after the signal S1. In practice, when the ultrasonic wave is propagated in the cladding of the fuel rod 1, part of the energy associated with these waves is transmitted to the water surrounding the cladding in which it is propagated in the form of compression waves with a lower speed than the propatation speed of the wave in the metal of the cladding.

The waves are reflected at the structures surrounding the fuel rod 1 and finally arrive at the sensor 5, which translates them into an interference signal S2.

The principal signal S1 is the result of the waves which are propagated in the cladding of the rod as far as the fissure 2 where they are scattered into the water in which the rod is immersed, before arriving at the sensor 5.

These scattered waves, which have a shorter path in the water than the waves reflected by the elements surrounding the rod 1, arrive at the sensor 5 before the reflected waves.

In the signal registered by the sensor 5, the part S1 of the signal therefore precedes the part S2 corresponding to the interference signals.

The form of the signal S1 scattered at the defect is established by calculation or measurement on an isolated rod, so that a window can be isolated, like that represented in the hatched part of FIG. 2, corresponding to the part of the ultrasonic signal scattered into the water at the defect.

During displacements of the sensors 5 in the direction Z, the signal S1 is shifted in time, since the path of the scattered waves in the water varies with the position Z of the sensor 5.

Accurate measurement of the position Z of the sensor 5 allows the position of the window corresponding to the signal S1 in the measured signal to be determined.

The maximum amplitude of the signal S1 is then measured and the variations in this maximum amplitude as a function of the position Z of the sensor 5 along the height of the rod are determined.

FIG. 3 shows the variation of this maximum amplitude as a function of the position of the sensor.

It is quite clear that in the case of a defect being present in the cladding of the rod, i.e., in the case of the existence of the scattered signal S1, the curve representing the variations A (Z) has a maximum at the value Z=ZO corresponding to the position of the sensor at the exact height of the defect 2.

The measuring and testing apparatus connected to the sensors 5, as shown in FIG. 1, consequently includes a preamplifier 7, a filter 8, an apparatus 9 for recording or displaying the signal A (t), after amplification and filtering, a filter 10 associated with a unit 11 for recording or displaying the window S1 of the signal filtered by the filter 10, and a unit 12 for determining the maximum amplitude A of the signal S1.

The apparatus also includes a unit 14 for measuring and recording the parameter Z determining the position of the sensor 5 over the height of the rods, a signal corresponding to this value of Z being transmitted to the filter 10 to determine the window corresponding to the signal S1 as a function of the position of the sensor.

Last, the apparatus includes a unit 16 for recording and/or displaying the signal A (Z) and determining the maximum of the curve A (Z).

The unit 16 receives on the one hand a signal representing the instantaneous value of Z and on the other hand the value of the maximum A of the signal S1 corresponding to this value of Z. The two values are recorded and allow recording and/or display of the curve A (Z).

Determination of the maximum of this curve when the sensor 5 is moved along the rod over its whole length allows determination of the value ZO corresponding to this maximum.

The apparatus therefore allows, on the one hand, determination of the presence of a defect in the rod 1 during examination and on the other, determination of the exact position of this defect on the rod.

In practice, the presence or absence of a scattered signal S1 in the signal picked up by the sensor 5 allows determination of a defective rod or a non-defective rod, respectively.

Accurate tracing of the curve A (Z) depends on the width of the window corresponding to the signal S1 in the signal picked up by the sensor 5.

Either calculating or display units can be used for the different units 9, 11 and 16, allowing determination and location of the defect by triggering of a signal associated with a numerical value, or by examination of a curve the maximum of which is determined.

In the case of a non-defective rod, the signal recorded and possibly displayed by the unit 9 is characterized of interference signals, including only a part S2. The signal is easily recognizable if calibration has previously been effected on a non-defective rod in a particular way, for example a new rod, put in a comparable environment.

When examination of an assembly is required, after an end plate has been removed allowing access to the end of each of the fuel rods of this assembly, a single sensor can be used, which is moved successively and automatically from one rod to another, or a set of ultrasonic emitters arranged in an array corresponding to the lattice of transverse sections of the rods in the assembly.

FIG. 4 shows diagrammatically such an apparatus used for testing an assembly 20 constituted by a set of rods 21 arranged in a square-mesh lattice in a transverse plane. A set of ultrasonic emitters 22 is disposed on a plate with approximately the dimensions of the end plate of the assembly which is positioned over this so that each of the emitters 22 is over a rod 21 and in contact with its upper cap.

An ultrasonic generator 23 is connected to each of the emitters 22 and associated with an electronic addressing apparatus allowing each of the emitters to be energized successively, i.e., ultrasonic waves to be sent successively into each of the rods 21 constituting the assembly.

X, Y addressing, for each of the rods of the assembly, in a transverse plane with respect to the assembly allows the fuel rod in which the ultrasounds are propagated to be identified.

The address of the emitter and the corresponding fuel rod is transmitted to a unit 26 which also receives the signal transmitted by a sensor 25 movable in the direction Z of the assembly, at a fixed distance from the side wall of the latter.

The assembly 20 is tested while the assembly is entirely immersed in the water of the fuel pond, and the sensor 25 is constituted by a bar of unit sensors the total length of which is at least equal to the side of the square constituting the transverse section of the assembly. In this way, the value of the signal received is increased because, when work on a rod disposed inside the assembly is involved, the wave scattered into the water is reflected at the components near the rod, so that the beam emitted outside the assembly has a greater width than that of a unit sensor, generally of the order of the side of the transverse section of the assembly.

The measuring and testing apparatus associated with the sensor 25 and the unit 26 is also like that described for a single fuel rod and represented in FIG. 1.

This apparatus includes a preamplifier 27, a filter 28, a unit 29 for recording and displaying the signal A (t), a filter 30 receiving a signal representing the measurement Z and allowing determination of the signal S1 and its recording and/or display in the unit 31 and a unit 32 for calculating the maximum of the amplitude A of the signal A (t).

This apparatus also includes a unit 34 for accurate measurement and development of a signal corresponding to the value of Z defining the position of the sensor 25 in the height dimension of the assembly and a unit 36 for recording and displaying the curve A (Z) and for determining the maximum of this curve corresponding to the value ZO defining the position of a possible defect in the rod during examination defined by its coordinates X, Y.

To give the apparatus extra sensitivity, instead of a single bar disposed near one of the faces of the assembly, a set of four bars entirely surrounding this assembly can be used.

The working of the apparatus represented in FIG. 4 is substantially identical to the working of the apparatus represented in FIG. 1, except that it allows identification of the defective rod or rods in an assembly by their coordinates X, Y. In practice, the coordinates X, Y can be identified at the unit 26, each time an ultrasonic signal scattered by a defect (S1) is identified on the curve A (t).

If no scattered signal is found for the whole of an assembly, such assembly can be considered non-defective.

One of the important advantages of the apparatus according to the invention is that it allows defective rods to be located with greater sensitivity than in prior techniques, since the signal picked up and undergoing discrimination is not drowned in the background noise of the signal produced in the rod, there being a time lag between the signal scattered by the defect and the background noise.

In addition, examination can be carried out while the assembly is immersed in a protective liquid, as is always the case for irradiated assemblies during storing or moving.

In addition, the detection method does not assume that the rod or the fuel assembly will be heated or that any other modification will be made in the physical conditions of the medium in which the assembly is immersed.

The method according to the invention also has the advantage of allowing all the rods to be examined, even those not at the periphery of the assembly, since, with those rods disposed within the assembly, the energy scattered by the possible defect travels to the sensor after reflection on the elements adjacent to that element disposed within this assembly.

In addition, the method according to the invention allows rods to be examined over their entire length and even in that part of them which is hidden by spacer grids, since the presence of the grids is translated simply into attenuation of the signal picked up which is compensated for by action on the amplitude of the signal emitted. In addition, the method according to the invention can be used on an assembly which has not been dismantled by using the free space between the caps of the rods and the upper plate for locating the sensors.

The invention is not, however, limited to the embodiment described; it includes all the variants thereof.

Thus, it is possible to use a fixed sensor positioned near the lateral surface of the rod or the assembly and receiving the waves which may be scattered into the water in which the rod or assembly is immersed by the defects thereof.

Of course, in this case, accurate locating of the defect will not be possible, but discrimination and filtering of the signal corresponding to the scattered waves are still possible by using a sensitive enough sensor disposed at a distance from the assembly, allowing both measurement and discrimination of the signal possibly associated with waves scattered into the water.

In the case of the testing of a complete assembly, instead of a bar of sensors corresponding in length to the length of the side of the assembly, a single sensor can be used, moved parallel to the side of the assembly's section so as to increase the extent of the region inspected.

In this instance, the sensor is moved both parallel to the axis of the assembly and in a direction perpendicular to that axis.

Use can also be made of a sensor which is moved inside guide tubes constituting the framework of the assembly instead of a sensor which is movable outside the assembly.

Lastly, different ways of effecting discrimination of the signal scattered into the water in which the fuel rod or assembly is immersed from those described can be envisaged.

The method and apparatus according to the invention is applicable to the detection and location of defects in any fuel assemblies constituted by fuel rods having a cladding within which the nuclear fuel is contained and which may have defects such as fissures.

We claim:

1. Method of detecting defective fuel elements in a nuclear reactor fuel assembly constituted by a bundle of elongate fuel rods disposed parallel to each other in the longitudinal direction of said assembly, said method comprising the steps of:
   (a) keeping said assembly entirely immersed in a protective liquid such as water;
   (b) emitting ultrasonic waves at one of the ends of each of said fuel rods successively and propagating said waves over the entire length of said fuel rod;
   (c) moving an ultrasonic sensor near the fuel rod in which said ultrasonic waves are propagated in its longitudinal direction, during propagation of the waves in said rod;
   (d) determining the presence of a defect in said rod by picking up, by means of said sensor, the ultrasonic waves eventually scattered by the defect in said rod into said protective liquid;
   (e) determining, when a defect is present, the variations of the amplitude of the signal picked up according to the position of said sensor in the longitudinal direction of said rod; and
   (f) determining the position of said sensor for which the amplitude of said signal is maximum corresponding to the position of the defect along the length of said rod.

2. Detection method according to claim 1, wherein said ultrasonic sensor (25) is moved outside said assembly (20).

3. Detection method according to claim 1, wherein said ultrasonic sensor (25) is moved inside said assembly in a guide tube thereof.

4. Detection method according to any one of claims 1, 2 or 3, comprising the step of filtering said signal as a function of the position of said sensor in the longitudinal direction to discriminate the waves eventually scattered by the defect from an interference signal due to interference waves propagated in said protective liquid and different from scattered waves, the time of propagation of said interference waves to said sensor being longer than the time of propagation of scattered waves.

5. Apparatus for detecting defective fuel elements in a nuclear reactor fuel assembly having fuel rods, comprising:
   (a) at least one ultrasonic emitter connected to a generator and to an addressing means allowing ultrasonic waves to be sent successively into each of said rods and allowing each rod subjected to said ultrasonic waves to be determined;
   (b) an ultrasonic sensor associated with means for its displacement in the longitudinal direction of said assembly;
   (c) means for measuring the longitudinal position of said sensor;
   (d) means for measuring the maximum amplitude of the signal corresponding to the waves scattered and detected by said sensor; and
   (e) means for determining the variations in said maximum amplitude as a function of the position of said sensor in the longitudinal direction of said assembly and for determining the position of said sensor corresponding to the maximum of the curve representing said variations.

6. Apparatus according to claim 5, comprising means for discriminating the signal corresponding to the scattered waves constituted by a filter (30) which takes into account the displacement in the time scale of the signal from the scattered waves as a function of the position of said sensor (25) by taking account of the effect of the position of said sensor (25) on the displacement in time of the signal corresponding to the scattered waves.

7. Apparatus according to claim 5 or 6, wherein said sensor (25) is movable in a direction perpendicular to the longitudinal direction of said assembly (20).

8. Apparatus according to claim 5 or 6, wherein said sensor (25) comprises unit detection elements assembled in a group constituting a bar arranged in a direction perpendicular to the longitudinal direction of said assembly (20) and having a length approaching that of the transverse section of said assembly (20).

* * * * *